United States Patent [19]

Ouriel et al.

[11] Patent Number: 4,952,215
[45] Date of Patent: Aug. 28, 1990

[54] VALVULOTOME WITH LEAFLET DISRUPTION HEADS AND FLUID SUPPLY

[75] Inventors: Kenneth Ouriel, Rochester; Karl D. Kirk; Donald Lamond, both of New York, all of N.Y.

[73] Assignee: Boisurge, Inc., Henrietta, N.Y.

[21] Appl. No.: 161,817

[22] Filed: Feb. 29, 1988

[51] Int. Cl.⁵ .............................................. A61B 17/32
[52] U.S. Cl. .................................. 606/159; 606/170; 604/22
[58] Field of Search .................. 128/305, 303 R, 311, 128/313, 309, 306, 751; 604/22, 159, 170, 191

[56] References Cited

U.S. PATENT DOCUMENTS

| | | | |
|---|---|---|---|
| 2,779,334 | 1/1957 | Sandborn | 128/303 |
| 3,837,345 | 9/1974 | Matar | 128/305 |
| 4,493,321 | 1/1985 | Leather | 128/305 |
| 4,655,217 | 4/1987 | Reed | 128/305 |
| 4,681,106 | 7/1987 | Kensey et al. | 128/305 |

FOREIGN PATENT DOCUMENTS

| | | | |
|---|---|---|---|
| 537676 | 1/1977 | U.S.S.R. | |
| 808082 | 3/1981 | U.S.S.R. | 128/305 |
| 2044103 | 10/1980 | United Kingdom | |

OTHER PUBLICATIONS

Kutz et al., "New Vein Stripper and Technique of Stripping", Surgery, Feb. 1951, pp. 271-275.

Skagseth et al., "In Situ Vein Bypass", Scand. J. Thor. Cardiovasc. Surg., 7:53-58, 1973.
Samuels et al., "In Situ Saphenous Vein Arterial Bypass", The American Surgeon, Feb. 1968, vol. 34, No. 2, pp. 122-129.
Mills et al., "Valvulotomy of Valves in the Saphenous Vein Graft Before Coronary Artery Bypass", J. Thorac.Cardiovasc. Surg., 76:878-879, 1976.
LeMaitre, In Situ Bypass Grafting, Vascutech, Inc., Andover, Mass., 1987, extracts including pp. 12-14, 24, 33-37, 47-54, 70-75, 87-93, 136-155.

Primary Examiner—Michael H. Thaler
Attorney, Agent, or Firm—Kenyon & Kenyon

[57] ABSTRACT

A valvulotome for rendering venous valve leaflets incompetent includes a rigid support comprising a fluid supply tube and, molded thereon, a dilator, and first and second valve disrupting heads. Each of the disrupting heads has a plane of symmetry, wherein the planes of symmetry of the two disrupting heads are relatively rotated by about 90°. A fluid emitting end of the fluid supply tube communicates with an irrigation port in a disrupting head so that fluid emitted through the irrigation port, during use, applies pressure to the valve leaflets to be disrupted. The other end of the fluid supply tube is swaged onto a catheter which in turn is coupled to a fluid supply source for the purpose of supplying fluid to the irrigation port.

15 Claims, 3 Drawing Sheets

VALVULOTOME WITH LEAFLET DISRUPTION HEADS AND FLUID SUPPLY

TECHNICAL FIELD

The invention relates to a valvulotome used in preparing a vein in situ for arterial bypass.

BACKGROUND ART

A well-recognized technique for arterial bypass has been the use of an in situ vein, such as the saphenous vein. Whereas arteries have smooth, unobstructed interior surfaces, veins have valves which ensure a primary direction of blood flow. The direction of blood flow in an artery is determined by the pumping action of the heart, i.e. the blood flow is away from the heart. On the other hand, the primary blood flow direction in a vein is directly opposite that, i.e. toward the heart. The valve typically is composed of two leaflets opposite each other. In response to blood flow away from the heart, the opposed edges of the leaflets are brought together to impede this blood flow. Thus if a vein is to be used as an arterial bypass, the valves must be rendered inoperative, for they would otherwise obstruct the arterial flow of blood. Techniques and devices for rendering valves inoperative are described in the following U.S. and foreign patent documents:

| Patent No. | Name |
|---|---|
| 2,779,334 | Sandborn |
| 3,837,345 | Matar |
| 4,493,321 | Leather |
| 4,655,217 | Reed |
| 4,681,106 | Kensey |
| USSR 537,676 | Shalimov |
| UK 2,044,103 | Ross | and in the following publications:

Kutz et al, "New Vein Stripper and Technique of Stripping", *Surgery*, February 1951, pp. 271 et seq;

Skagseth et al, "In Situ Vein Bypass", *Scand J Thor Cardiovosc Surg*, 7:53–58, 1973;

Samuels, "In Situ Saphenous Vein Arterial Bypass", *The American Surgeon*, February 1968, Vol. 34, No. 2, pp. 122 et seq;

Mills, "Valvulotomy of Valves in the Saphenous Vein Graft Before Coronary Artery Bypass", *J. Thorac. Cardiovasc. Surg.*, 76: 878–879, 1976; and LeMaitre, *In Situ Bypass Grafting*, 1987.

Leather describes that it "has been found that the simplest, most expedient and least traumatic method of rendering the bicuspid venous valve incompetent is to cut the leaflets in their major axes while they were held in the functionally closed position by fluid flow or arterial pressure from above."

In order to accomplish this purpose, Leather describes that it is necessary to expose both proximal and distal sites of the vein. The proximal site is closer to the heart than the distal site. A rod is inserted through the distal incision and through the vein until it exits at the proximal incision. A valve cutter is attached to the rod and a catheter is sutured to the valve cutter. The valve cutter is then drawn into the vein through the proximal incision. Fluid supplied by the catheter keeps the valve leaflets closed during the retrograde motion of the cutter through the vein, i.e. from proximal to distal sites.

The Russian Patent No. 537,676 describes a similar instrument.

Some of the valve cutters or valvulotomes use instruments of cylindrical form to render the valves inoperative. These instruments are designed to ride within the vein and disable the valve leaflets around their entire circumferential junction with the vein wall. Other valvulotomes use valve disrupting elements of planar form, e.g. Leather 4,493,321. A disadvantage of the planar form of instrument is that it is necessary to properly orient the instrument for maximum effectiveness. When the instrument is in use (within the vein) the surgeon is not in a position to visually observe the orientation relative to the valve leaflets. It is therefore another object of the present invention to provide a valvulotome in which the orientation of the disrupting element relative to the valve leaflets is no longer crucial for the effective operation of the instrument.

SUMMARY OF THE INVENTION

The invention meets these and other objects by providing a valvulotome with an integral fluid supply which can be inserted within a vein at a single incision site, which traverses smoothly past several valves in the vein and then during a retrograde motion effects the valve disrupting or disabling action. The valvulotome of the invention may have two heads, each including a valve disrupting element of planar form where the orientations of the two elements are rotated with respect to each other by about 90°.

More particularly, a valvulotome in accordance with the invention includes a rigid support, at least one disrupting head mounted on the support with a disrupting surface arranged for disrupting action during retrograde motion of the valvulotome, the support including a fluid supply tube with a fluid outlet, the fluid supply tube extending into the disrupting head and having a fluid outlet to supply fluid to a location after the disrupting head has passed that location during the retrograde motion of the valvulotome. In other words, relative to the disrupting head the fluid outlet is located so that fluid pressure provided has the same direction as pressure that would be supplied by the heart. In the presence of valve leaflets, this pressure causes the leaflets to stand up for effective disrupting action by the disrupting element or head during the retrograde motion.

In accordance with another aspect of the invention, the valvulotome of the invention includes two disrupting heads, both mounted on the support where the second disrupting head is located on the support and positioned ahead of the first disrupting head during the retrograde motion. In accordance with the invention, the orientation of the disrupting heads are rotated with respect to each other by about 90°.

The valvulotome of the invention also may include a vein dilator also located on the rigid support and located to contact a valve leaflet before the valve leaflet is contacted by either of the first or the second cutting head, during the retrograde motion. The dilator serves to dilate the vein and maintain the valvulotome aligned along the axis of the vein for effective disrupting action.

The invention is also directed at a method of manufacturing a valvulotome such as is described above. In accordance with this aspect of the invention, a hollow tube or cannula, preferably stainless steel for example 20 gauge, is provided with first and second ends, the second end comprises an irrigation port and the first end is flanged so that it can be swaged onto a catheter. The second end (irrigation port) may also be flanged so the cannula has a symmetric appearance. The cannula has several locations on its outer circumference which are knurled. Other types of circumferential surface discontinuities, aside from those effected by knurling, may also be used. The flanged end is swaged onto a catheter, for example a spiral wound stainless steel flexible catheter. The tube or cannula is located within a mold including at least three separate compartments. A first compartment of the mold is arranged for the molding of a first disrupting head having a generally planar leaflet disrupting element. A second compartment of the mold is arranged for the molding of a second disrupting head also having a generally planar disrupting element where the disrupting element of the second head is rotated by about 90° with respect to the disrupting element of the first head. The third compartment of the mold is arranged for molding a dilator or guide and at the same time providing a permanent attachment between the supply tube and catheter. The mold is filled with a suitable plastic, e.g. polypropylene, polystyrene or polyethylene, and the two heads and dilator are molded onto the tube. After completion of the molding operation, the assembly of the tube now supporting the dilator and the first and second heads is removed from the mold. The catheter has an end opposite to the end to which the assembly has been swaged which includes a coupling adapted for coupling the catheter to a fluid source.

Thus in accordance with this aspect the invention provides a method of manufacturing a valve cutter comprising the steps of:

(a) providing a hollow tube,
(b) attaching said tube to a catheter,
(c) molding onto said hollow tube at least two bodies, a first body comprising a valve disrupting head with at least a generally planar valve disrupting element, and a second body comprising a vein dilator.

The method of the invention may also include a further step of molding a third body onto the hollow tube located between the first body and the second body, the third body comprising another valve disrupting head with a valve disrupting element wherein the valve disrupting element of the third body is rotated approximately 90° with respect to the valve disrupting element of the first body.

BRIEF DESCRIPTION OF THE DRAWINGS

The present invention will now be further described in such detail, when taken in conjunction with the attached drawings, as to enable those skilled in the art to make and use the same. In the attached drawings like reference characters identify identical apparatus and moreover.

DETAILED DESCRIPTION OF PREFERRED EMBODIMENTS

Figure 1:
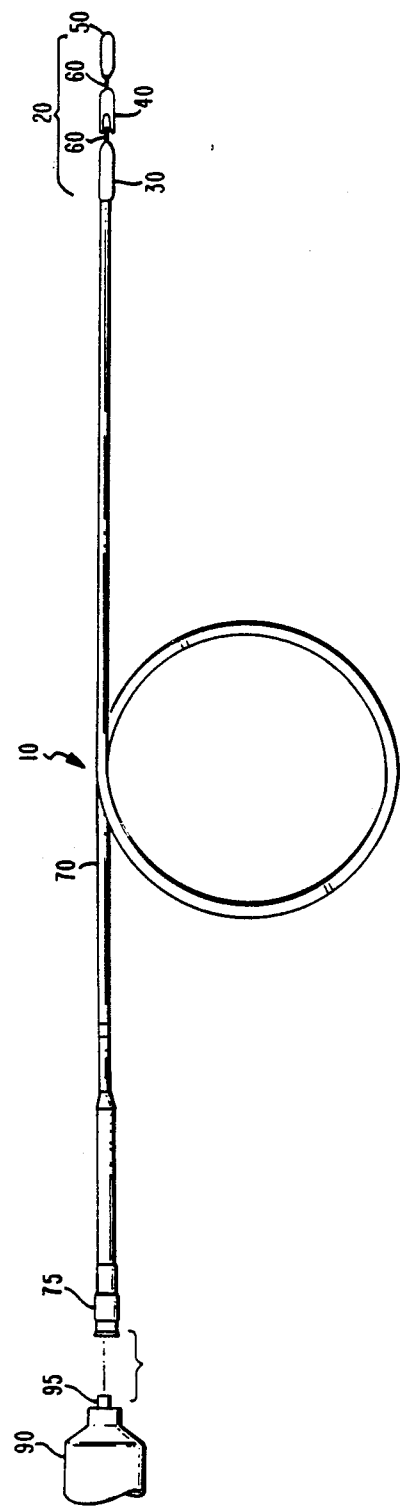
FIG. 1 is an illustration of the valvulotome of the invention assembled for actual use.

FIG. 1 is a view of the valvulotome 10 of the present invention assembled for use. The valvulotome 10 comprises two components, a valvulotome assembly 20 and a catheter 70. The valvulotome assembly 20 is located at one end of the catheter 70, and the other end of the catheter 70 includes a fluid supply coupling 75, such as the female half of a luer-lock. Also shown in FIG. 1 is a fluid source 90 including the male half of the luer-lock 95. The fluid coupling 75/95 and the catheter 70 are conventional components; the catheter for example can be a spiral wound stainless steel flexible catheter. The valvulotome assembly 20 includes three major components, all supported on a rigid support comprising a fluid supply tube 60. The three major components include a dilator 30 with two ends, both of which are relatively streamlined, a first disrupting head 40 which is streamlined at a first end and has a disrupting element located at the opposite end and a second disrupting head 50 also includes a streamlined end, and an opposite end including a disrupting element.

Figure 2:
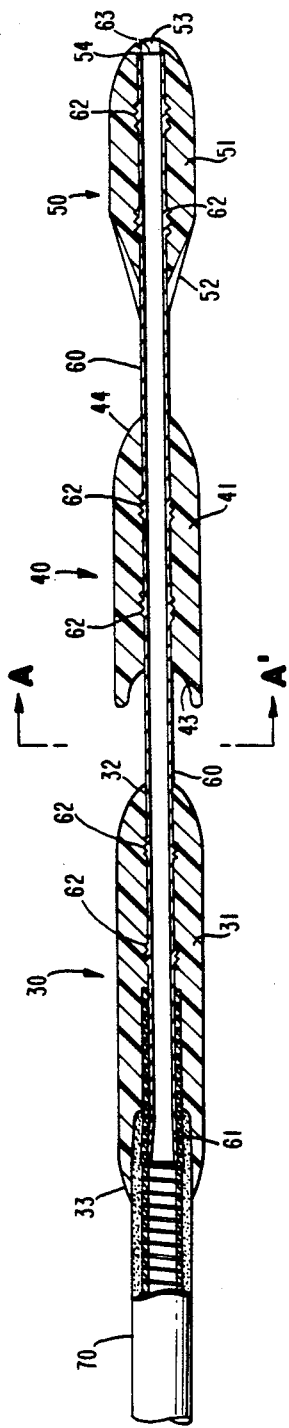
FIG. 2 is a section of the valvulotome assembly 20.

FIG. 2 is a section of the valvulotome assembly 20. More particularly, and as shown in FIG. 2, the dilator 30 includes a dilator body 31 supported on a rigid support comprising a fluid supply tube 60 which may for example be a 20-gauge stainless steel cannula. The fluid supply tube 60 has a first end 61 which is flanged so that it can be swaged onto a free end of the catheter 70. The cannula is knurled at several locations 62. The dilator body 31 includes a streamlined first end 32 and a streamlined second end 33. The dilator body can be insert-molded polypropylene, polystyrene or polyethylene or of other suitable material. The action of molding the dilator body 31 overlying the swaged end of cannula 60 provides a permanent attachment between catheter and tube 60.

The fluid supply tube 60 also supports a first disrupting head 40. The disrupting head 40 includes a disrupting head body 41 having a first streamlined end 44 and a second disrupting element 43. The disrupting element 43 will be described in more detail below in connection with FIGS. 3 and 4. The disrupting head body 41 is molded onto the fluid supply tube 60 encompassing one or more knurled locations 62.

The valvulotome assembly 20 includes a second disrupting head 50 having disrupting body 51 with a streamlined free end 54 and a disrupting element 52. The fluid supply tube 60 terminates in a fluid supply end 63 and a passageway in the body 51 communicates between the fluid supply end 63 and an irrigation port 53 in the disrupting head 50. The disrupting head body 51 is molded onto the fluid supply tube 60 encompassing one or more knurled locations 62.

As shown in FIG. 2 the first disrupting head 40 is mounted on the fluid supply tube 60 to be intermediate between the second disrupting head 50 and the dilator 30.

In use, the valvulotome assembly is inserted through an appropriate incision into a vein below (that is further from the heart than the location of the valve leaflets to be rendered incompetent), and passed through the vein in a direction to travel past the valve leaflets to be rendered inoperative. During this first or forward motion, the streamlined first ends 54, 44 and 32 enable the components of the valvulotome assembly to readily travel past the valve leaflets to be rendered incompetent. Once the entire valvulotome assembly has been inserted so as to pass each of the valve leaflets to be rendered incompetent, the fluid supply source 90 is manipulated to pump fluid through the fluid supply tube 60 and out the irrigation port 53. The pressure caused by the introduction of this fluid is applied to the valve leaflets, forcing them to stand up in a condition where they can be readily disrupted. At this point the valvulotome assembly is drawn, with a retrograde motion, back in the direction toward the incision. During this motion, the disrupting heads 43 and 52 are operative to disrupt the valve leaflets and render them incompetent.

Each of the disrupting heads 40 and 50 has a disrupting element (which will be described hereinafter) which defines a plane. Further, the disrupting heads 40 and 50 are arranged so that a theoretical plane passing through both the longitudinal axis of tube 60 and a disrupting element of one head is rotated by about 90° with respect to another theoretical plane passing through the longitudinal axis of the tube 60 and a disrupting element of the second head. As a result, the angular orientation of the valvulotome assembly 20 relative to the valve leaflets to be rendered inoperative less critical than it was in prior art arrangements which included only a single disrupting head.

Once the valvulotome assembly has traveled, in its retrograde motion, past each of the valve leaflets, it can be removed from the vein.

Figure 3:
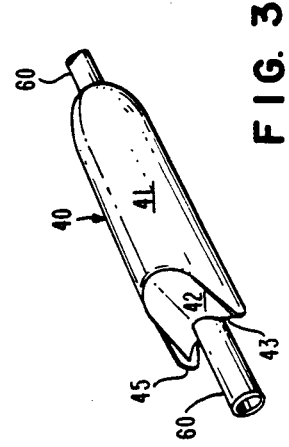
FIG. 3 is an isometric view of one of the disrupting heads.

FIG. 3 shows an isometric view of the first disrupting head 40, and its relation to the fluid supply tube 60 on which it is supported. The disrupting element includes a pair of guides 45 and located therebetween a disrupting surface 43. The disrupting surface 43 is formed at the convergence of a pair of converging surfaces 42, the theoretical plane which has been referred to is that plane bisecting the fluid supply tube along its longitudinal extent and passing through the disrupting surface 43. A similar plane, also bisecting the fluid supply tube 60 along its longitudinal extent passing through the disrupting surface of the second disrupting head 50, lies at an angle of about 90° with respect to the plane associated with the first disrupting head 40.

Figure 6:
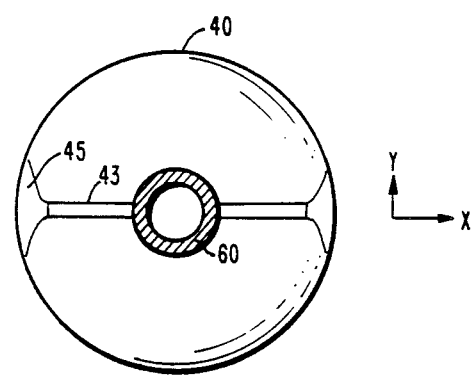
FIG. 6 is a section taken on the line A—A' of FIG. 2.

FIG. 6 is the section A—A' of the first cutting head 40 showing the fluid supply tube 60, the disrupting surface 43 and the guides 45.

The valvulotome assembly 20 is manufactured as follows. A suitable fluid supply tube 60 is selected and knurled at the locations 62 (FIG. 2). The selection of the location and spacing of the knurled locations 62 is determined by their purpose, i.e. to secure the molded bodies of the valvulotome assembly 20 against movement relative to the tube 60. One end of the fluid supply tube 60 is flanged as shown at 61. A suitable catheter 70 is swaged onto the flanged end 61 of the fluid supply tube 60. A mold is provided for each of the elements of the valvulotome assembly including the dilator body 30, the first disrupting head 40 and the second disrupting head 50. Alternatively, a single mold can be provided with a separate compartment for each of the elements 30, 40 and 50. The fluid supply tube 60 is inserted into the mold with its free end 63 located within the compartment or the mold designed to form the second disrupting head 50. The mold is filled with suitable plastic material such as polypropylene, polystyrene or polyethylene and allowed to cure forming the valvulotome assembly 20 onto the fluid supply tube 60. When curing is complete the entire assembly can be removed from the mold.

Figure 4:
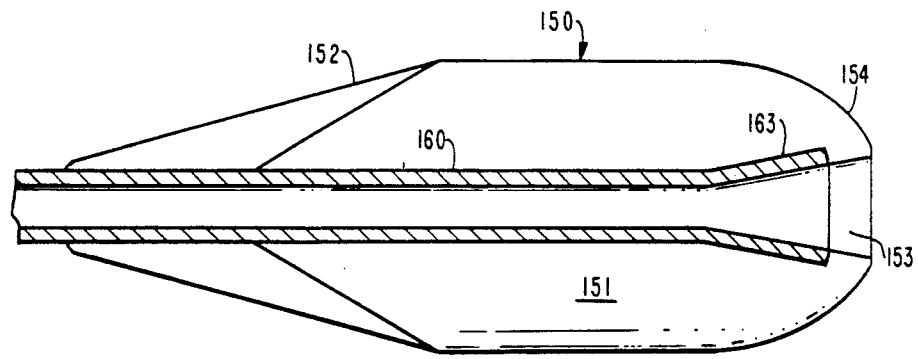
FIG. 4 is a section of another form for a head similar to head 50 of the disrupting heads.
Figure 5:
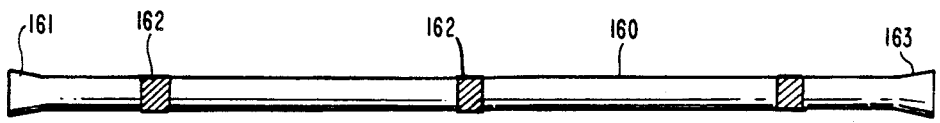
FIG. 5 is a plan view of a different but preferred suitable hollow tube or cannula 160.

FIGS. 4 and 5 show respectively a section of a disrupting head 150 which is slightly different in form, but similar in function to the disrupting head 50. FIG. 4 shows that the disrupting head 150 includes a body 151 having a streamlined end 154 having a port 153 therein. The other end of the body 151 has a valve disrupting surface 152, so that when the valvulotome assembly 20 is drawn in the retrograde direction, the surface 152 acts to disrupt or disable valve leaflets. The difference between the disrupting head 150 and that of disrupting head 50 is that the cannula 160 has a flanged end 163 communicating with the port 153.

FIG. 5 is a plan view of a different but preferred form of suitable hollow tube or cannula 160. The cannula 160 has, as is seen in FIG. 5, flanged ends 161 and 163. In addition, the cannula 160 has knurled locations 162. In the embodiment of the hollow tube 160 shown in FIG. 5, there is one knurled location 162 for each of the bodies to be molded on the cannula. In the form shown in FIG. 5 the cannula 160 is symmetrical about an axis bisecting the middle one of the three knurled locations 162.

It should be apparent that various changes can be made within the spirit and scope of the invention, especially with respect to various specific parameters which have been disclosed in connection with the preferred embodiment such as the fluid supply tube 60, the material for the various disrupting heads and the catheter. While knurling has been suggested for integrally securing the molded bodies to the tube 60, those skilled in the art will realize that other equivalent techniques can be used. Although we have specified a catheter separate from the fluid supply tube, it is conceivable that, with a catheter of appropriate form, the separate cannula can be dispensed with. The invention thus meets the objects by providing for a fluid supply source which supplies fluid to a location, after than location has been past by the disrupting heads during a retrograde motion, so that the valve leaflets are forced to stand up for effective disruption. Furthermore, the use of two disrupting heads which are offset relative to each other by about 90° renders the orientation of the valvulotome assembly during the operation less critical than it had been in the prior art which employed only a single head.

We claim:

1. A valvulotome for rendering various valve leaflets incompetent comprising:
    a rigid support
    a first disrupting head mounted on said support with a disrupting surface mounted for disrupting action during retrograde motion of said valvulotome,
    said rigid support comprising a fluid supply tube having a fluid outlet, said fluid supply tube extending into said disrupting head so that said fluid outlet supplied fluid to a location during a retrograde motion with respect to the direction of blood flow after said disrupting head has initially passed said location; and
    a second disrupting head located on said support and positioned ahead of said first disrupting head during said retrograde motion.

2. A valvulotome as recited in claim 1 which further includes a dilator mounted on said support and positioned ahead of said first disrupting head during said retrograde motion.

3. A valvulotome as recited in claim 2 wherein said fluid supply tube extends trough said second disrupting head, said dilator and into said first disrupting head.

4. A valvulotome as recited in claim 1 wherein said fluid supply tube includes a flanged end and a catheter coupled to said flanged end.

5. A valvulotome comprising a cannula having a first flanged end and a second flanged end, said cannula including at least three spaced regions, each of said regions including machined surface discontinuities, two of said three spaced regions located adjacent a different one of said flanged ends,
- a first valve leaflet disrupting head integrally mounted on said cannula and encompassing one of said surface discontinuity including regions adjacent said first flanged end, said valve disrupting head including first and second ends, a first end including an irrigation port communicating with said flanged end of said cannula, and a second end, opposite said first end, including a valve leaflet disrupting surface,
- a second valve disrupting head integrally supported on said cannula superimposed on that one of said surface discontinuity including regions not adjacent either of said flanged ends, said second valve leaflet disrupting head including a first, streamlined end and a second, valve leaflet disrupting end, opposite said first end,
- a vein dilator integrally supported on said cannula adjacent one of said surface discontinuity including regions adjacent said second flanged end and extending beyond said second flanged end, said dilator including a first streamlined end and a second streamlined end,
- a catheter with a first end swaged onto said second flanged end of said cannula and located within said vein dilator, and a fluid coupling located on another end of said catheter.

6. The valvulotome of claim 5 wherein said first and second valve disrupting heads have planes of symmetry, a plane of symmetry of a first valve disrupting head rotated about 90° with respect to a plane of symmetry of said second valve disrupting head.

7. A method of manufacturing a valvulotome comprising the steps of:
  (a) providing a hollow cannula,
  (b) attaching said cannula to a catheter,
  (c) molding onto said hollow cannula at least two bodies, a first body comprising a valve disrupting head with at least one disrupting element and a fluid outlet communicating with a fluid outlet of said hollow cannula, and a second body comprising a dilator, said second body spaced from said first body along said cannula; and
  (d) molding a third body onto said hollow cannula located between said first body and said second body, said third body comprising another valve disrupting head with a valve disrupting element.

8. A method as recited in claim 7 which includes a step of providing said catheter with a free end having a fluid coupling.

9. A method as recited in claim 7 wherein prior to said step (c) an outer surface of said cannula is distorted.

10. A method as recited in claim 9 wherein said surface distortion is effected at least at one location encompassed by each of said bodies.

11. A valvulotome for rendering venous valve leaflets incompetent comprising:
  a rigid support,
  a first disrupting head mounted on said support with a disrupting surface mounted for disrupting action during a retrograde motion, with respect to the direction of blood flow, of said valvulotome,
  a dilator mounted on said support and positioned ahead of said first disrupting head during said retrograde motion,
  a second disrupting head located on said support and positioned between said first disrupting head and said dilator,
  said rigid support comprising a fluid supply tube having a fluid outlet, said fluid supply tube extending through said second disrupting head, said dilator, and into said first disrupting head so that said fluid outlet supplies fluid to a location during said retrograde motion after said first and second disrupting heads have initially passed said location,
  said first and second disrupting heads each having an axis of symmetry wherein said axis of symmetry of said first disrupting head is rotated relative to said axis of said second disrupting head by about 90 degrees.

12. A valvulotome for rendering venous valve leaflets incompetent comprising:
  a rigid support,
  a first disrupting head mounted on said support with a disrupting surface mounted for disrupting action during a retrograde motion, with respect to the direction of blood flow, of said valvulotome,
  said rigid support comprising a fluid supply tube having a fluid outlet, said fluid supply tube extending into said first disrupting head so that said fluid outlet supplies fluid to a location during said retrograde motion after said disrupting head has initially passed said location,
  said fluid supply tube further including a flanged end and a catheter coupled to said flanged end,
  said first disrupting head being integrally mounted on said fluid supply tube,
  a second disrupting head integrally mounted on said fluid supply tube and positioned ahead of said first disrupting head during said retrograde motion,
  a dilator mounted on said fluid supply tube and positioned ahead of said first disrupting head during said retrograde motion,
  wherein said first and second disrupting heads each having an axis of symmetry wherein said axis of symmetry of said first disrupting head is rotated relative to said axis of said second disrupting head by about 90 degrees.

13. A valvulotome for rendering venous valve leaflets incompetent comprising:
  a rigid support,
  a first disrupting head mounted on said support with a disrupting surface mounted for disrupting action during retrograde motion, with respect to the direction of blood flow, of said valvulotome,
  said rigid support comprising a fluid supply tube having a fluid outlet, said fluid supply tube extending into said first disrupting head so that said fluid outlet supplies fluid to a location during said retrograde motion after said disrupting head has initially passed said location,
  said fluid supply tube further including a flanged end and a catheter coupled to said flanged end,
  said first disrupting head being integrally mounted on said fluid supply tube,
  a second disrupting head integrally mounted on said fluid supply tube and positioned ahead of said first disrupting head during said retrograde, motion, a dilator mounted on said fluid supply tube and positioned ahead of said first disrupting head during said retrograde motion, said first and second disrupting heads each having an axis of symmetry wherein said axis of symmetry of said first disrupting head is rotated relative to said axis of said second disrupting head by about 90 degrees, and wherein said fluid supply tube is circumferentially knurled at one or more locations which are encompassed by said first and said second disrupting heads and said dilator.

14. A method of manufacturing a valvulotome for rendering venous valve leaflets incompetent comprising the steps of:
   (a) providing a hollow cannula,
   (b) attaching said cannula to a catheter,
   (c) molding onto said hollow cannula three bodies; a first body comprising a valve disrupting head with at least one disrupting element and a fluid outlet communicating with a fluid outlet of said hollow cannula;
      a second body comprising a dilator, said second body spaced from said first body along said cannula; and a third body located between said first body and said second body, said third body comprising another valve disrupting head with a valve disrupting element, and
      said first and third bodies being molded onto said hollow cannula so that each includes an axis of symmetry wherein said axis of symmetry of one of the disrupting heads of said first or third bodies is rotated, relative to an axis of symmetry of the other disrupting head of said first or third bodies, by about 90 degrees.

15. A method of manufacturing a valvulotome for rendering venous valve leaflets incompetent comprising the steps of:
   (a) providing a hollow cannula;
   (b) attaching said cannula to a catheter,
   (c) distorting an outer surface of said cannula at least at one location encompassed by each of said bodies,
   (d) molding onto said hollow cannula three bodies,
      a first body comprising a valve disrupting head with at least one disrupting element and a fluid outlet communicating with a fluid outlet of said hollow cannula;
      a second body comprising a dilator, said second body spaced from said first body along said cannula;
      a third body located between said first and second body, said third body comprising another valve disrupting head with a valve disrupting element and wherein said surface distortion is effected at a location encompassed by said third body.

* * * * *